United States Patent
Pattern et al.

(10) Patent No.: US 7,335,156 B2
(45) Date of Patent: Feb. 26, 2008

(54) DIGITAL ELECTROMAGNETIC PULSE GENERATOR

(76) Inventors: Ernest Paul Pattern, 1590 NW. Third St., Deerfield Beach, FL (US) 33442; Luis Alberto Rovedo, Lambare 1088, Buenos Aires (AR)

( * ) Notice: Subject to any disclaimer, the term of this patent is extended or adjusted under 35 U.S.C. 154(b) by 78 days.

(21) Appl. No.: 11/397,749

(22) Filed: Apr. 4, 2006

(65) Prior Publication Data

US 2006/0224215 A1    Oct. 5, 2006

Related U.S. Application Data

(60) Provisional application No. 60/667,980, filed on Apr. 4, 2005.

(51) Int. Cl.
*A61N 1/00*    (2006.01)

(52) U.S. Cl. ................... 600/14

(58) Field of Classification Search .......... 600/9–15
See application file for complete search history.

(56) References Cited

U.S. PATENT DOCUMENTS

| | | | |
|---|---|---|---|
| 4,197,851 A | 4/1980 | Fellus | |
| 4,454,883 A | 6/1984 | Fellus | |
| 5,224,922 A * | 7/1993 | Kurtz | ............ 600/13 |
| 5,441,495 A * | 8/1995 | Liboff et al. | ............ 600/9 |
| 5,480,373 A * | 1/1996 | Fischer et al. | ............ 600/14 |
| 6,029,084 A | 2/2000 | Long et al. | |
| 6,167,304 A | 12/2000 | Loos | |
| 6,641,520 B2 * | 11/2003 | Bailey et al. | ............ 600/9 |
| 2003/0045770 A1 * | 3/2003 | van Mullekom | ............ 600/9 |
| 2005/0182288 A1 * | 8/2005 | Zabara | ............ 600/14 |

FOREIGN PATENT DOCUMENTS

GB        2156679 A    10/1985

* cited by examiner

*Primary Examiner*—Samuel G Gilbert
(74) *Attorney, Agent, or Firm*—Charles J. Prescott

(57) ABSTRACT

Method and apparatus are provided for therapeutic administration to body parts digitally generated electromagnetic fields with trapezoidal, square, triangular and sawtoothed and other complex temporal field waveforms that are microcontroller controlled for a range of amplitude, frequency, and dc offsets; the apparatus providing programmed sequences of radiation waveforms. Multiple electromagnetic antennas establish a variety of field configurations for exposure of various body parts in the treatment of a wide range of afflictions including exfoliation of calcium deposits causing improvements in arthritis and other rheumatic diseases—osteoarthritis, nervous interconnection (neuropathies), etc., the treatment of tremors and seizures, migraine, hypertension, lower back pain, urinary incontinence, and premenstrual tension. Temperature sensors within the antennas are provided to limit the temperatures therein.

9 Claims, 6 Drawing Sheets

DIGITAL ELECTROMAGNETIC PULSE GENERATOR

CROSS-REFERENCE TO RELATED APPLICATIONS

This application claims the benefit of U.S. Provisional Application No. 60/667,980 filed Apr. 4, 2005 entitled "Digital Electromagnetic Pulse Generator," the entire content of which is expressly incorporated herein by reference.

STATEMENT REGARDING FEDERALLY SPONSORED RESEARCH OR DEVELOPMENT

Not applicable

INCORPORATION-BY-REFERENCE OF MATERIAL SUBMITTED ON A COMPACT DISC

Not applicable

BACKGROUND OF THE INVENTION

1. Field of the Invention

This invention relates generally to medical equipment for Magnetic Resonance Therapy (MRT), and more specifically to electromagnetic therapy for reduction of symptoms and for curing a large variety of physical and mental conditions.

2. Description of Related Art

There is abundant history of magnets being used for medical treatment. In 440 BC, Socrates utilized magnetite in the treatment of menstrual disorders. Magnetite is a member of the spinel group of minerals which has the standard formula $A(B)2O4$. The A and B usually represent different metal ions that occupy specific sites in the crystal structure. In the case of magnetite, $Fe3O4$, the A metal is Fe +2 and the B metal is Fe +3; two different metal ions in two specific sites. This arrangement causes a transfer of electrons between the different irons in a structured path or vector. This electric vector generates the magnetic field. Common present day systems utilize electric currents through conductive coils to flexibly generate variable magnetic fields spatially and temporally.

In 1857 Dr. Al Pulvermacher of Vienna introduced an "Electromagnetic Belt" in England. More recently, Fallus, in U.S. Pat. No. 4,197,851, issued on Apr. 15, 1980, utilizes magnetic fields applied to a patient through the application of an electrode to the body for electrotherapeutic treatment. In Fallus' U.S. Pat. No. 4,454,883, issued on Jun. 19, 1984, weak electromagnetic fringe fields are employed for the control of tremors and seizures, and disorders of the autonomic nervous system such as panic attack.

Loos, in U.S. Pat. No. 6,167,304, issued on Dec. 26, 2000, teaches an apparatus for manipulating the nervous system using an external electric field with variable pulse parameters, and Long, et al. in U.S. Pat. No. 6,029,084, issued on Feb. 22, 2000, utilizes electromagnetic fields in synchronization with the heart, and in an earlier UK Patent GB-2156679-B, issued on Sep. 16, 1987, offers relief for migraine, hypertension, lower back pain, and premenstrual tension. No prior art has been found for electromagnetic therapy using digitally generated unipolar magnetic fields, nor with temperature control of the electrodes.

Magnetic Resonance Therapy (MRT) involves the use of electromagnetic fields applied to the body for beneficial effects. The buildup of calcium phosphate and calcium carbonate in the cells of the body contribute to degradations in teeth, joints, heart, etc. Since calcium molecules are paramagnetic they align and become cemented together as stones, granulomas, and plaque. The application of periodic oscillatory magnetic fields to regions of the body loosens the calcium molecular bonds allowing these deposits to free and exfoliate into the blood stream for removal by the kidneys.

Magnetic therapy has become a standard medical treatment for many conditions or diseases in Eastern Europe, Asia and former USSR countries. Magnetic therapy is an innovative, emerging medical technology, with an extensive biological research base. For example: the use of MRT in the healing of non-union fractures, and in nerve conduction testing.

The roots of this bioscience come from the studies done in biomagnetics, the study of the body's own magnetic fields. All human activity is conditioned by the earth's magnetic environment, and in the last two decades biomedical knowledge has advanced dramatically in the area of bioelectricity, not only in nerve conduction but also in electrolytic phenomena.

Magnetic forces exist in the space around moving electrical particles, which can affect other moving particles. The source of these forces can be electrons in wires where electric current flows, ions in electrolytic solutions, electrons in cathode ray tubes, etc. The static magnetic field around permanent magnets is based on the same principle. In the permanent magnet, motion of electrons (spin and orbital motion moment) is arranged such that "magnetic field" forces exist outside of the magnet as magnetic flux.

Magnetic fields can be classified according to their space attributes as uniform or non-uniform. Uniform fields are those where in every point of the field area of interest substantially the same value (strength and sign) and direction is exhibited, such as the condition of a static passive magnet or electromagnet with direct current (DC) flowing therein. In current magnetic therapy applications non-uniform fields are generally used.

In time varying magnetic fields, magnetic flux density or intensity changes with time, typically periodic at specific frequencies. Time varying magnetic fields result from electromagnets fed with non-constant currents, e.g. alternating (AC) currents. The most common varying fields are found around electrical wires conducting AC current, such as to electrical appliances.

Magnetic fields are characterized by intensity (H) and magnetic flux density (B). The intensity of a magnetic field is directly proportional to the current flowing through a wire and indirectly proportional to the distance from the wire:

$$H = I/2\pi r$$

Where I=current intensity in amperes, r=distance from the wire in meters. The unit of H is ampere/meter (A/m) defined as the intensity of a magnetic field at a distance r=½ n from the wire wherein a current of 1 A is flowing.

Magnetic flux density is measured in units of Tesla (T). This unit is defined as follows: if a force acting on a wire 1 meter long with 1 A flowing in a uniform magnetic field is 1 N (Newton), this field has the magnetic flux density of 1 T.

A field of one Tesla is quite strong: the strongest fields available in laboratories are about 20 Teslas, and the Earth's magnetic flux density, at its surface, is about 50 microteslas (μT).

An alternate unit of magnetic flux is gauss (G), where 1 G=10-4 T (0.0001 T), 1 T=$10^4$ G.

The relation between B and H is given as follows:

$$B = \mu H$$

Where $\mu$ is the environment permeability. The relation $\mu = \mu r$. $\mu o$ is used, where $\mu r$ is relative permeability and $\mu o$ is the permeability of a vacuum. In biological systems permeability is close to that of air and therefore $B \approx H$.

There are three established physical mechanisms through which static and time-varying magnetic fields interact with living matter.

Magnetic Induction: relevant to both static and time varying magnetic fields, originates through the following interactions:

1. Electrodynamic interactions with moving electrolytes are based on Lorenz forces on moving ionic charge carriers and thus electric fields and currents are induced. This type of interaction is the basis of magnetically induced blood flow potentials that have been studied with both static and time varying magnetic fields.
2. Faraday currents—relevant to time varying magnetic fields only. Most scientists consider this interaction as the key mechanism of magnetic therapy with time varying magnetic fields.
3. Magnetomechanical Effects: relevant mainly to static magnetic fields: In uniform magnetic fields, both diamagnetic and paramagnetic molecules experience torque, which tends to orient them in a configuration that minimizes their free energy within the field. When the fields used for magnetic therapy are relatively weak (10 to 100 mT), a magnetomechanical action may not be significant. Magnetomechanical translation can be found in high gradient static magnetic fields that leads to the motion of either paramagnetic or ferromagnetic particles. This action may not be a significant contributor of magnetic therapy effects.
4. Electronic Interactions: seen with static fields but may also be relevant to time varied fields: Some chemical reactions are based on an action on radicals. In these circumstances static magnetic fields exhibit an effect on electronic spin states. It is possible that, although the lifetimes of the intermediates caused by this interaction are short, they can still be a sufficiently strong influence on biological matter via changed kinetics of dynamic chemical reactions.

Faraday's Law and Current Density

Generally, time varying magnetic fields, versus static fields, have been useful for therapeutic purposes since it is most commonly believed that if the key mechanism of action is induction of electrical currents, the appropriate approach is the use of time varying magnetic fields. In accord with Faraday's law, magnetic fields that vary in time will induce potentials and circulating currents in biological systems, including the human body. Current density can be estimated using following formula:

$$J = E.\sigma = n r 2 / 2 n r. dB/dt. \quad \sigma = \sigma r/2.dB/dt$$

For sinusoidal fields a simplified equation is appropriate:

$$J = n.r.f.\sigma.B$$

Where J=current density $(A/M^2)$
E=induced potential (V/M)
r=radius of the inductive loop (M)
$\sigma$=tissue conductivity (S/M)
dB/dt=rate of change of magnetic flux density It has been determined that current density up to 100 $mA/M^2$ is safe. From this viewpoint, to assure maximum safety we consider the highest conductivity of tissue, i.e. 0.2 S/m. However, this calculation is more theoretical than practical since the human body constitutes many tissues with differing conductivity values. This is the primary reason why we cannot calculate exactly the level of induced currents in the complicated, non-homogenous structures of the body.

Prior art MRT devices provide analog drive signals and analog electromagnetic fields, which are inefficient and result in excessive generation of heat. An object of the present invention is to provide efficient apparatus for the generation of electromagnetic waves utilizing digital electronics and providing magnetic waveforms with a variety of waveform patterns, and a thermal limiter or shutoff circuit when temperatures exceed a predetermined threshold.

BRIEF SUMMARY OF THE INVENTION

This invention is directed to Digital ElectroMagnetic Resonance Therapy and provides efficient and flexible generation of magnetic fields for application to the body for a variety of therapeutic uses. The Digital ElectroMagnetic Pulse Generator (DEMP) of the present invention provides a selection from a plurality of waveforms, all generated digitally for the efficient creation of magnetic fields. The DEMP is useable with a variety of antennas, such as copper-coil electromagnets, well known in the art, for generating magnetic waveforms from the electrical current supplied thereto. Magnetic Resonance Therapy consists of the application of one or more antennas to different parts of the body. It requires that the antennas face each other to compliment each other's magnetic potentials. The north side of one must face the south side of the antenna on the same channel. It is important that the North-South axis of the antennas face the East-West geographic direction for maximum cell resonance.

It is therefore an object of this invention to provide efficient and flexible generation of magnetic fields for application to the human body for a variety of therapeutic uses.

In accordance with these and other objects which will become apparent hereinafter, the instant invention will now be described with reference to the accompanying drawings.

BRIEF DESCRIPTION OF THE SEVERAL VIEWS OF THE DRAWING(S)

DETAILED DESCRIPTION OF THE INVENTION

Figure 1:
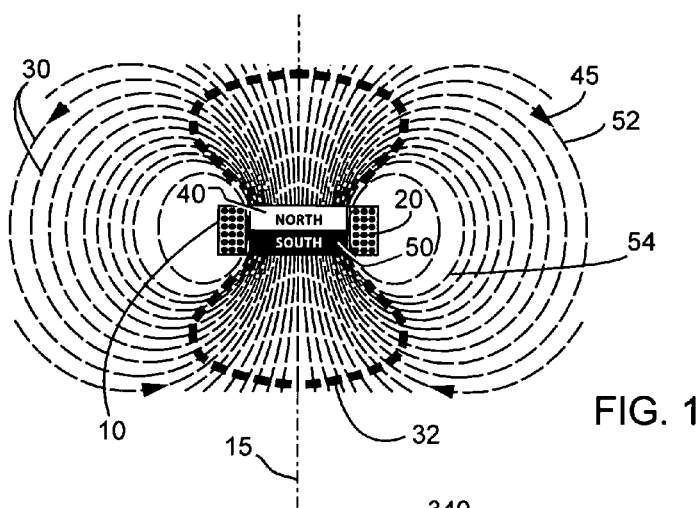
FIG. 1 is a cross sectional plan view of the magnetic flux of an air-core electromagnetic antenna also showing a high-field region cross section.

FIG. 1 illustrates magnetic flux lines 30 emanating from a single air core antenna coil 10 wound with a substantial number of turns of electrical wire, preferably copper, with coil windings 20 arranged in a generally concentric pattern. When energized with electric current, the coil forms an electromagnet with a NORTH magnetic pole 40 and a SOUTH magnetic pole 50 having a region of relatively high flux density in a high-field region 32. By convention of magnetic flux direction, flux lines such as outboard flux line 52 flow from NORTH to SOUTH indicated by flux direction arrow 45. Inner flux line 54 originates near the inner diameter of coil 10 whereas outboard flux line 52 originates from a location closer to the axis 15 of coil 10.

Figure 2:
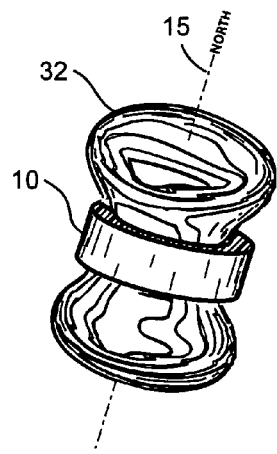
FIG. 2 is a perspective view of the high-field region surface.

FIG. 2 is a three-dimensional representation of the electromagnet high-field region 32 depicted as a surface that illustrates the depth of penetration of the high-field region. At surface 32 all flux within that solid boundary is of an intensity value greater than at the surface, and provides a graphic indication of the relative penetration of an arbitrary level of magnetic flux relative to the size of coil 10.

Figure 3:
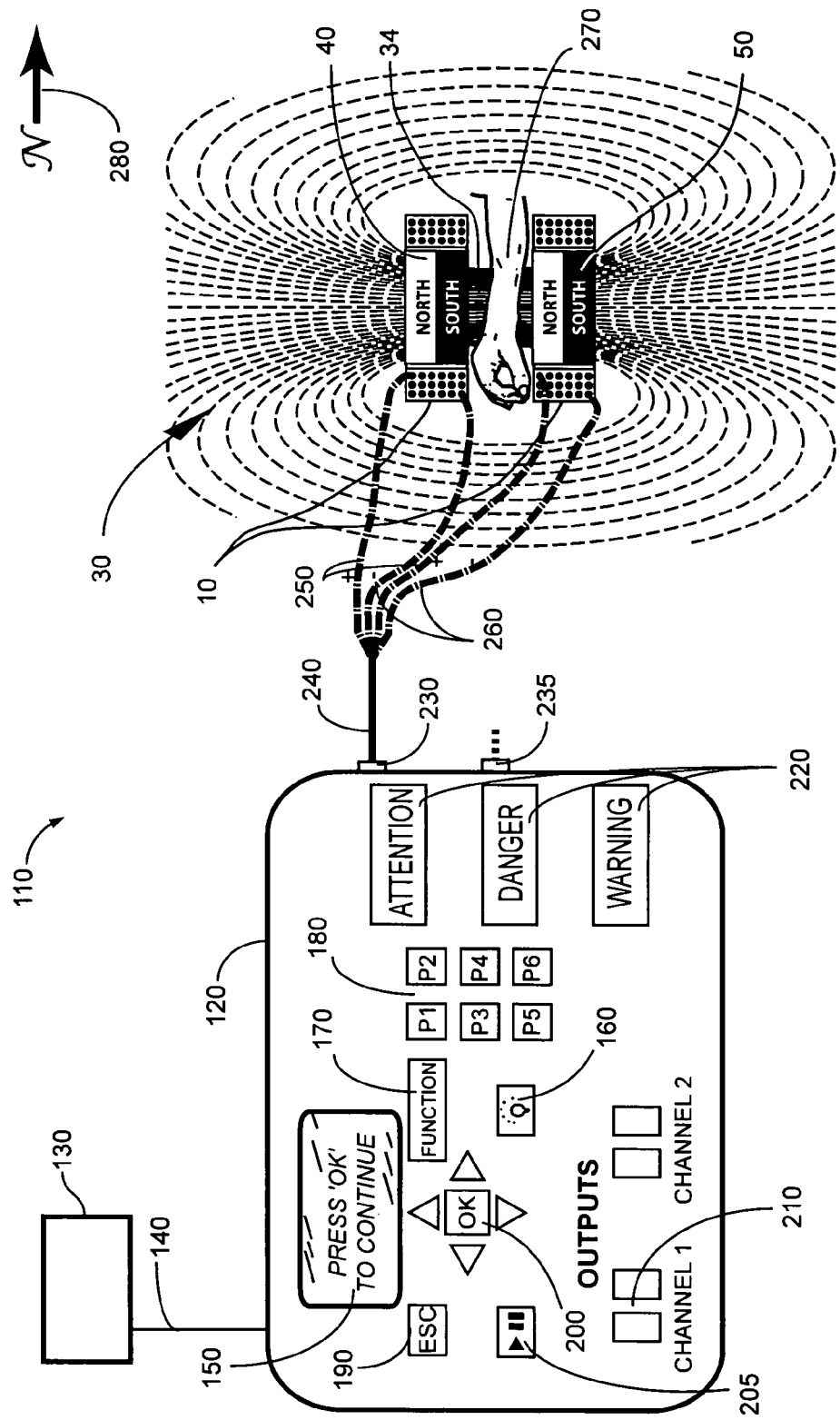
FIG. 3 is a functional diagram of a DEMP system of the invention in use.

FIG. 3 illustrates a preferred embodiment of the instant invention Digital ElectroMagnetic Pulse Generator (DEMP) system 110, including power source 130, power connection 140, DEMP control unit 120, antenna cable 240, connected to two antenna coils 10. The two antenna coils are preferably arranged on opposing sides of a patient's arm 270 to create, upon excitation, two electromagnets and cause a strong magnetic field illustrated by magnetic flux lines 34 to pass therethrough. Electrical current flowing into coils 10 through source conductors 250 and returning through return conductors 260 create North poles 40 and South poles 50. When the amplitude of current flow changes, a varying magnetic field is created within the patient's arm 270 to create therapeutic Faraday currents within the arm. Although two antenna coils are shown, a plurality of antenna pairs may be employed, and may be oriented in a variety of orientations within the scope of the invention. It is preferable to orient antenna coils 10 such that the axis of field lines 15 is normal to earth's magnetic north direction 280. Coil construction follows methods well known in the art, including copper wire wound upon a plastic mandrel, wrapped with insulating tape, not shown, for strain relief and durability. Standard soldering and insulating methods are used to connect the conductors to the coil windings. Temperature sensor 35 is incorporated within the antenna assembly to reliably monitor and limit internal antenna temperature, and may be attached to the coil with commonly used epoxy adhesive.

DEMP control unit 120 includes electronics described below, display 150, Escape pushbutton 190, Operate and Pause button 205, five push-button navigation switches 200, function push-button 170, power button 160, and six program buttons 180 for commanding specific electromagnetic field sequences of waveform shape and complexity and in predetermined sequence programs as described below. Channel lamps 210 and notification lamps 220 provide operational feedback to the operator. The display, pushbuttons, navigation switches, and power source are all common elements in modern electronic devices, with mechanical and electrical characteristics well known to those skilled in the art. DEMP control unit 120 includes two channels (one illustrated in detail) for connection to two pairs of antenna coils 10 through connectors 230 and 235.

Figure 4:
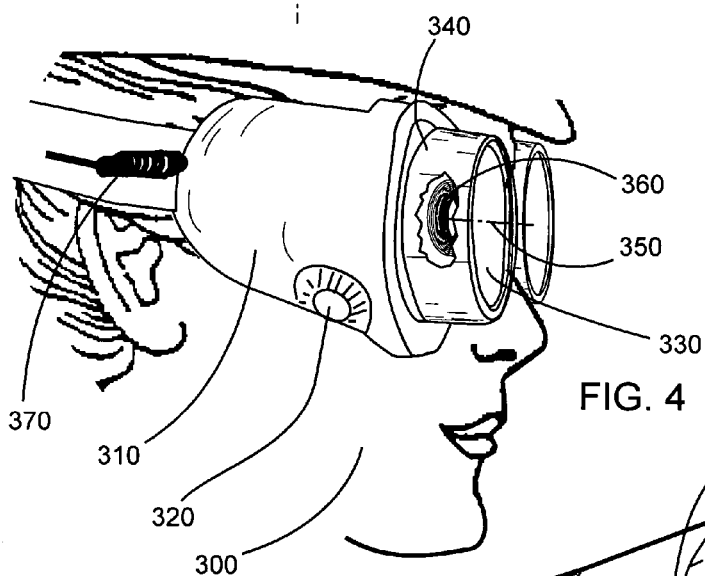
FIG. 4 is perspective diagram of the DEMP system in use with ocular antenna goggles.

FIG. 4 illustrates a preferred embodiment ocular goggles 310 for treatment of diseases of the eye, with air core ocular coil 360 allowing patient 300 vision therethrough along magnetic axis 350 during therapy sessions. Tehe DEMP control unit is set to 250 watts, and is used to treat retinitis pigmentosa, retinal degeneration, senile macular degeneration, retinal dystrophy, neuropathy on optic nerves, corneal trauma, corneal perforation, glaucoma simplex, atrophy of the optic nerve, etc. Cover 340 holds protective pane 330; air vent 320 prevents excess humidity internal to the goggles. An antenna capacity of 7 watts per eye is appropriate to produce the maximum movement. Cord connector 370 interconnects ocular coil 360 to the DEMP control unit. Goggles 310 are constructed with structural plastics and cushioning fabrics well known in the art. Temperature sensors, not shown, are incorporated within the goggles in close proximity to ocular antenna coils 360 to monitor and limit internal antenna temperature.

Table I provides electrical and mechanical characteristics of preferred embodiment antenna coils of the invention for connection to the DEMP control unit, and indicates the number of coils used. Multiple antenna coils such as intracranial 12 may be connected in series/parallel arrangements to be adapted to the DEMP control unit driver capacity.

Figure 5:
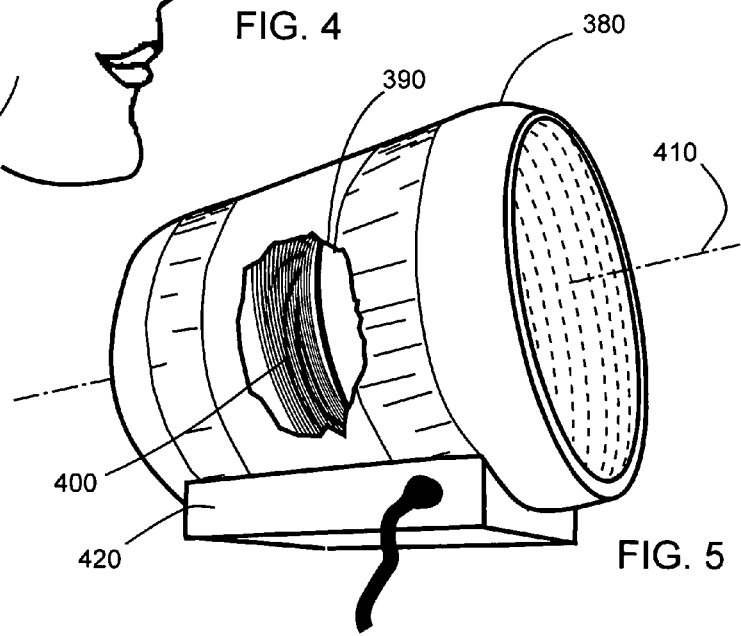
FIG. 5 is a perspective diagram of a tunnel antenna

FIG. 5 is a single-coil tunnel antenna 380 with coil 400 illustrating a large air core center for generating magnetic flux along axis 410. Table I lists three tunnel antenna sizes. The larger tunnel is for the legs. The smaller tunnels are used for the arms. The tunnels are used to treat various bone injuries, fractures, burns, carpal tunnel syndrome, limb grafts, infected skin wounds, rheumatic/Musculoskeletal diseases, etc. Generally approximately 500 watts is applied from the DEMP generator. A temperature sensor, not shown, is in close proximity to the antenna coil to monitor and limit internal antenna temperature, and may alternatively be located within support housing 420.

TABLE I

Preferred Antenna Coil Characteristics

| Antenna Use | Number of Coils | Antenna Wire Gauge, mm | Internal Diameter, mm | External Diameter, mm | H, Turns | Core |
|---|---|---|---|---|---|---|
| Intra-cranial 6 | 6 | 0.15 | 10 | 24 | 31 | Air |
| Intra-cranial 8 | 8 | 0.15 | 10 | 24 | 31 | Air |
| Intra-cranial 12 | 12 | 0.15 | 10 | 24 | 31 | Air |
| Intra-cranial 16 | 16 | 0.15 | 10 | 24 | 31 | Air |
| Tunnel/LARGE | 1 | 0.75 | 245 | 250 | 67 | Air |
| Tunnel/MEDIUM | 1 | 0.65 | 197 | 200 | 102 | Air |
| Tunnel/SMALL | 1 | 0.40 | 110 | 113 | 70 | Air |
| Ocular | 2 | 0.25 | 10 | 45 | 38 | Air |
| Urology | 1 | 1.00 | 90 | 206 | 14 | Air |
|  | 2 | 0.50 | 25 | 100 | 25 | Air |
| Full Body | 3 | 1.50 | 410 | 500 | 15 | Air |
| Full Body Opponent | 1 | 1.50 | 410 | 500 | 15 | Air |
| Local 30 W | 2 | 0.35 | 25 | 60 | 40 | Air |
| Local 60 W | 2 | 0.50 | 25 | 100 | 25 | Air |
| Local 100 W | 2 | 0.75 | 60 | 145 | 19 | Air |
| Facial | 4 | 0.25/0.35 | 10 | 24/45 | 31/38 | Air |
| Cervical | 2 | 035 | 25 | 60 | 40 | Air |
| Lumbar | 2 | 0.35 | 25 | 60 | 40 | Air |

Figure 6:
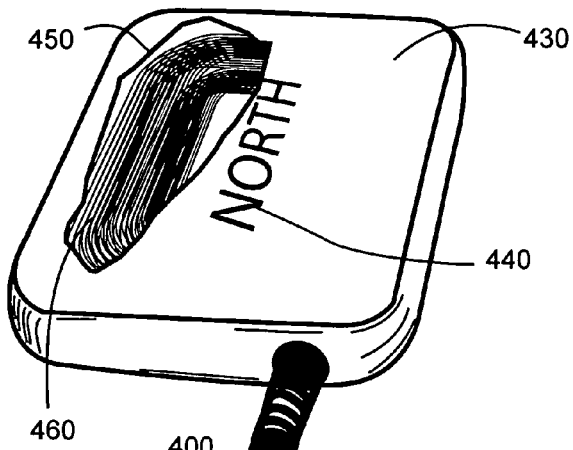
FIG. 6 is a perspective diagram of a paddle antenna.

FIG. 6 illustrates the construction of a generic antenna paddle 430 illustrating coil 460 visible through drawing cutout 450 and interconnection 400 for coupling to the DEMP control unit. Since paddles may be used in various numbers and configurations, it important to consistently label paddles with polarity labels indicating NORTH 440 and SOUTH 445 (in FIG. 7) to insure proper placement with respect to all antenna paddles in use for a specific therapy. Paddle 430 includes an internal temperature sensor, not shown, to monitor and limit antenna coil temperature. The temperature sensor measurement is useable in the DEMP control unit to modify generated current waveforms as described below.

Figure 7:
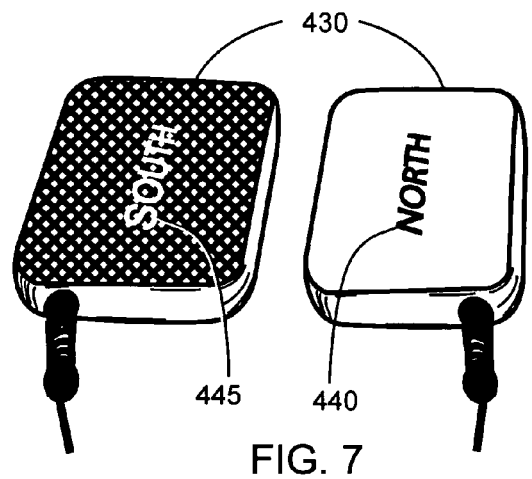
FIG. 7 is a perspective diagram of two paddle antennas oriented side-by-side.
Figure 8:
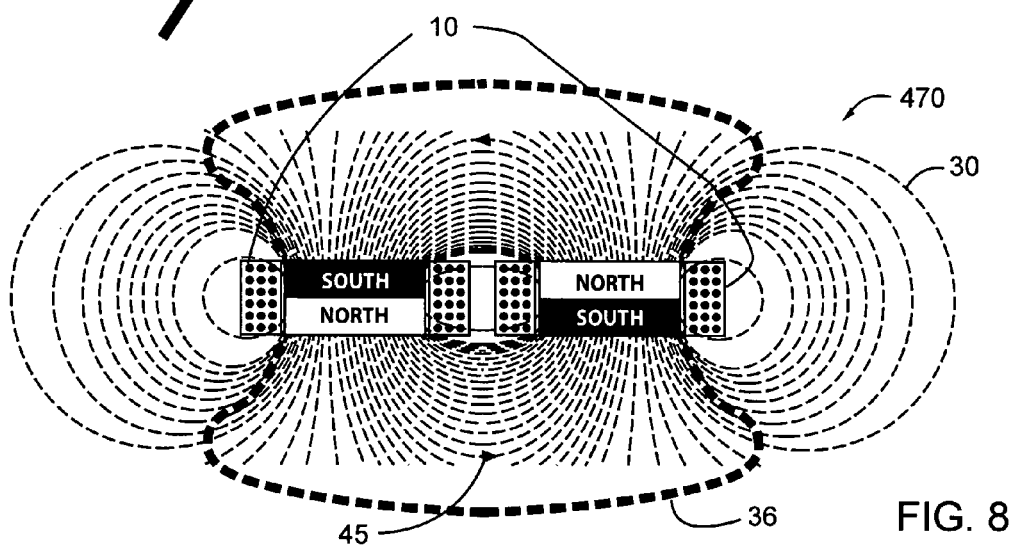
FIG. 8 is a cross sectional plan view of the two-paddle antenna of FIG. 7 illustrating the magnetic field lines.

FIG. 7 illustrates a typical planar orientation of two antenna paddles 430 with NORTH 440 and SOUTH 445 labels to create a deep high-field region 36 illustrated in the magnetic flux cross sectional diagram 470 of FIG. 8, which indicates flux lines 30 created by the two coils 10. Note that high-field region flux lines are common to both coils and flow in the direction 45 from NORTH to SOUTH.

Figure 9:
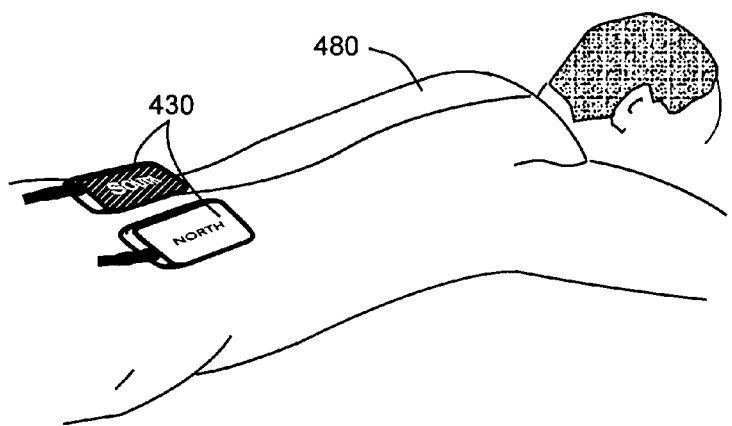
FIG. 9 is a perspective drawing of a two-paddle application for lumbar therapy.

FIG. 9 illustrates the antenna paddle 430 pair of FIGS. 7 and 8 applied to a patient 480 in a lumbar therapy treatment in which diseased or strained internal areas are exposed to high-field regions of the antenna magnetic flux to cause Faraday currents to flow therein. Multiple paddle pairs, not shown, are useful for upper back therapies. Full body treatment utilizes 5000 watts from the DEMP generator and is used to treat peripheral vascular diseases, liver function, heart disease, hypertension, lung diseases, gastrointestinal diseases, etc.

Figure 10:
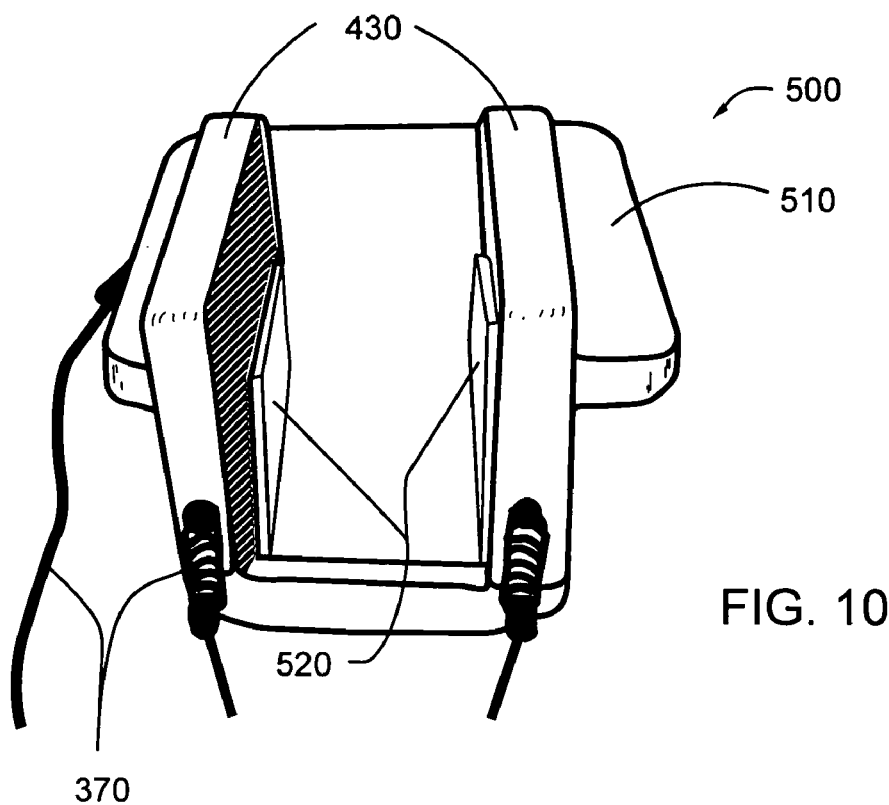
FIG. 10 is a perspective drawing of a urinary antenna ensemble.

FIG. 10 illustrates a urinary/countenance therapy antenna set 500, including buttocks paddle 510 and two side paddles 430 in storage fixture 520. Urinary antenna cables 370 interconnect to the DEMP control unit set to 1000 watts. The pelvic floor cells are excitable in multiple directions by virtue of the locations of the antennas. Buttocks antenna 510 also includes an internal temperature sensor, not shown, to monitor and limit antenna coil temperature.

Figure 11:
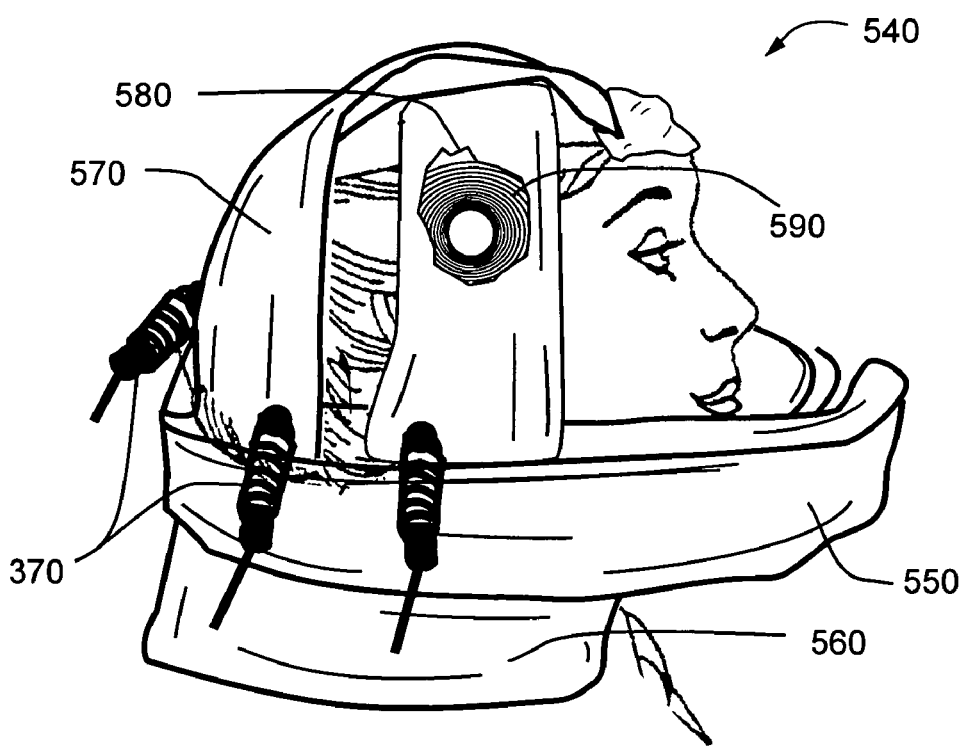
FIG. 11 is a perspective drawing of a cranial antenna in use.

FIG. 11 illustrates an intra-cranial antenna helmet 540, which includes neck structure 560, chin structure 550, and cranium structure 570 alignment elements of the helmet. Drawing cutout 580 exposes intra-cranial antenna coil 590, which interconnects through cables 370 to the DEMP control unit set to 3 to 5 Hz and 30% to 90% power. This preferred embodiment is used to treat neurological diseases, brain neurosecretion, Parkinson's disease, etc. Helmet 540 is constructed with plastic structural supports as described above, with fabric liners commonly known in the art. Helmet 540 includes internal temperature sensors, not shown, to monitor and limit antenna coil temperatures.

Figure 13:
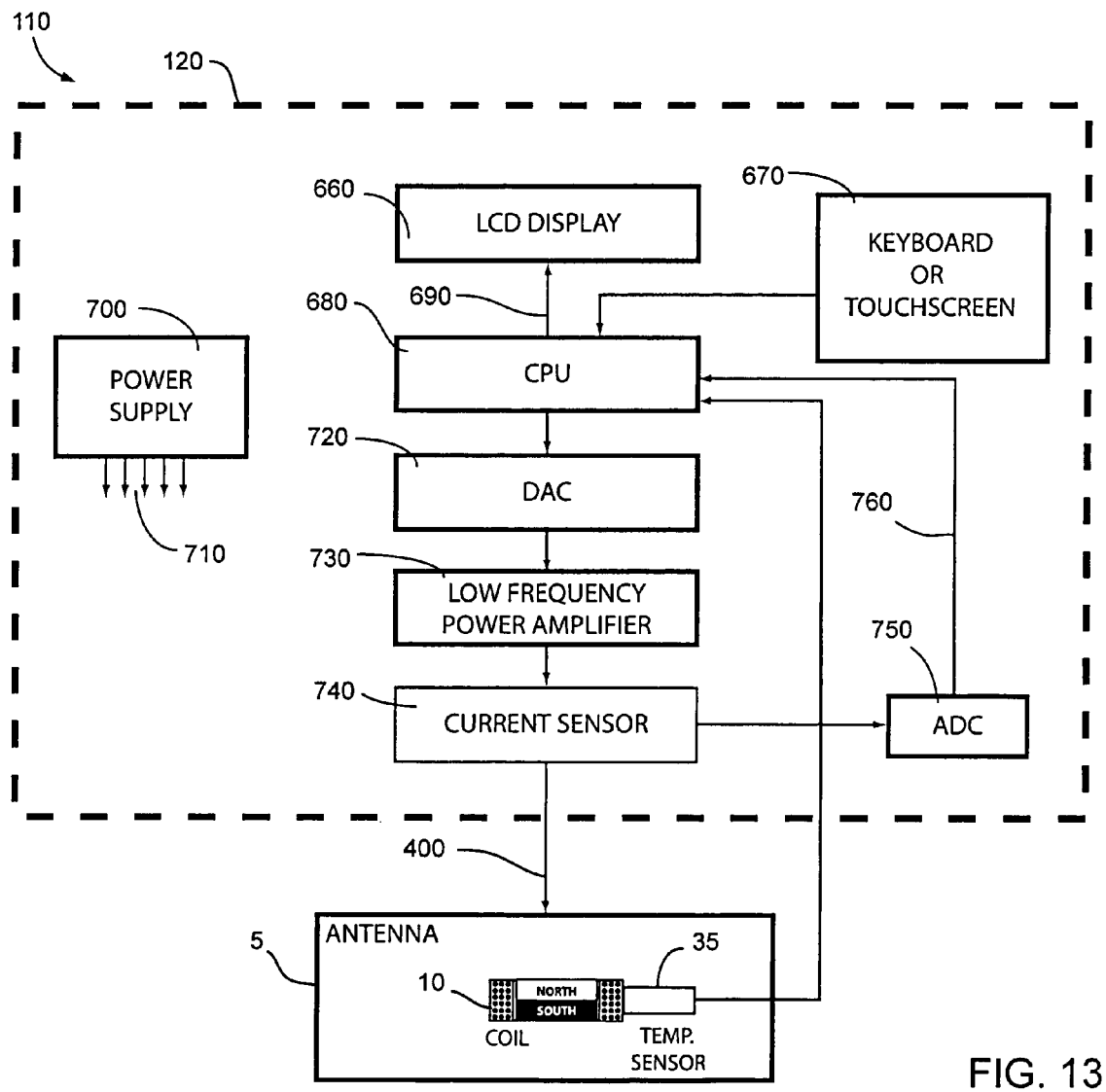
FIG. 13 is a functional block diagram of the electronic elements of the system.

FIG. 13 is a functional block diagram of a DEMP system 110 of the invention. Power supply 700 within DEMP control unit 120 provides a variety of power forms 710 for connection within the electronics. LCD display 660 is driven through a typical bus interconnect 690 by Central Processor Unit (CPU) electronics 680. The CPU receives current feedback signals from ADC 760 and from temperature sensor 35, and drives Digital to Analog Converter (DAC) 720. The DAC 720 in turn drives Low Frequency Power Amplifier 730 supplying the antenna coil current, which is monitored by current sensor 740 through output connection 240. CPU 680 may be an integrated circuit microcontroller such as an 8-bit RISC microcontroller manufactured by ATMEL. LCD Display 660 may be DMF-50773 manufactured by OPTRIX, which may include touch screen 670 integrated therein. DAC 720 may be MAX5891 manufactured by MAXIM, or equivalent. Power Supply 700, amplifier 730, and ADC 760 are common electronic components commonly known in the art, and software algorithms associated with CPU 680 are well known in the art for generating waveform, sequence programs, and controls described above.

FIGS. 14, 15, 16, and 17 illustrate graphical plots of amplitude 800 vs. time 610 of four exemplary alternate trapezoidal output waveforms for generating a variety of temporally varying electromagnetic fields with five time duration portions of period "T" 880. Amplitudes are normalized to a common peak value, whereas it should be understood that the peak amplitudes are controllable and adjustable by the operator and by the predetermined program sequences. Each of the four illustrated trapezoid waveforms is created with five temporal periods totaling the full period "T" 880. Optimal waveforms are chosen as a function of antenna, power, and frequency configuration. The waveform portion "D" 860 is a negative peak and its length depends on the inductance of the antenna used and its discharge slope. The waveform portion "E" 870 is set sufficient for substantially all inductive energy dissipation prior to the next cycle.

Figure 14:
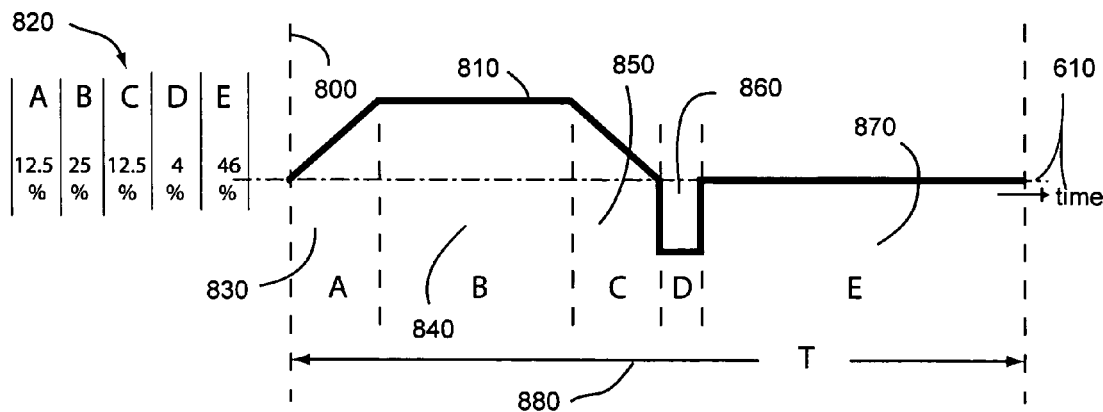
FIG. 14 is a drawing of the basic time graph with a trapezoid wave output embodiment of the system.

Referring to FIG. 14, standard trapezoid wave 810 is generated by programming A time duration 830, B time duration 840, C time duration 850, D time duration 860, and E time duration 870. Standard trapezoid time duration table 820 provides time percentages of waveform period T 880 for said standard trapezoid wave 810. Various amplitudes, periods, T 880, and sequences are programmable in the DEMP control unit described above and further described in the functional block diagram of FIG. 13.

Figure 15:
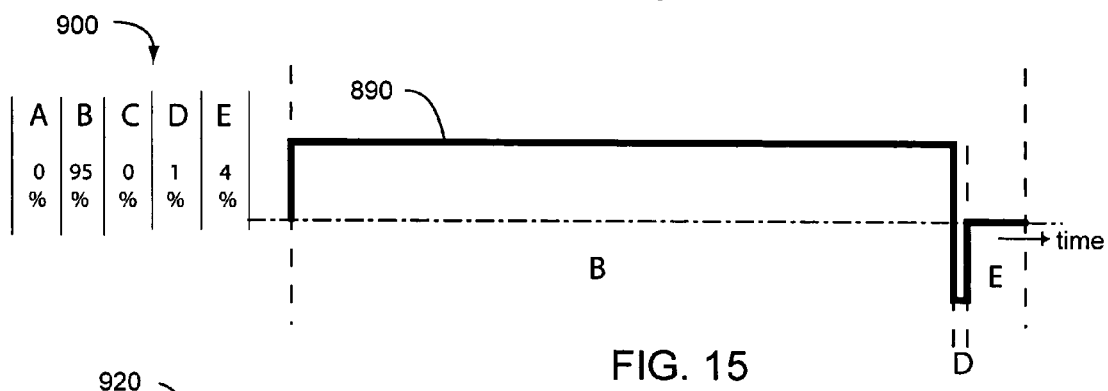
FIG. 15 is a drawing of an alternate time graph of a square wave output embodiment of the system.
Figure 16:
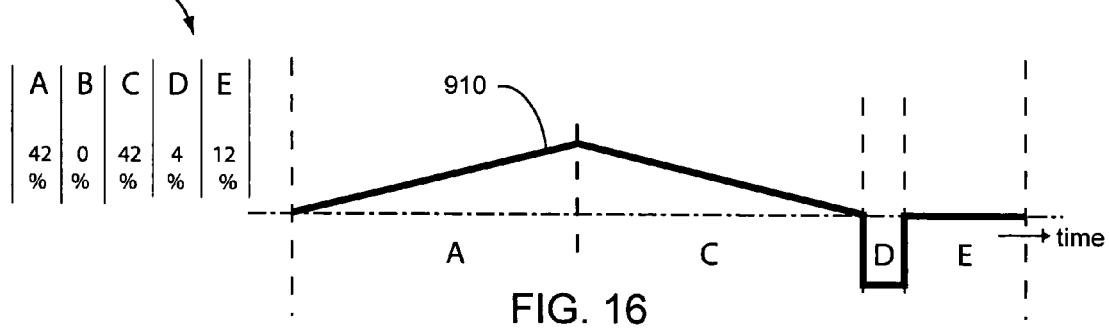
FIG. 16 is a drawing of a third alternate time graph of a triangular wave output embodiment of the system.
Figure 17:
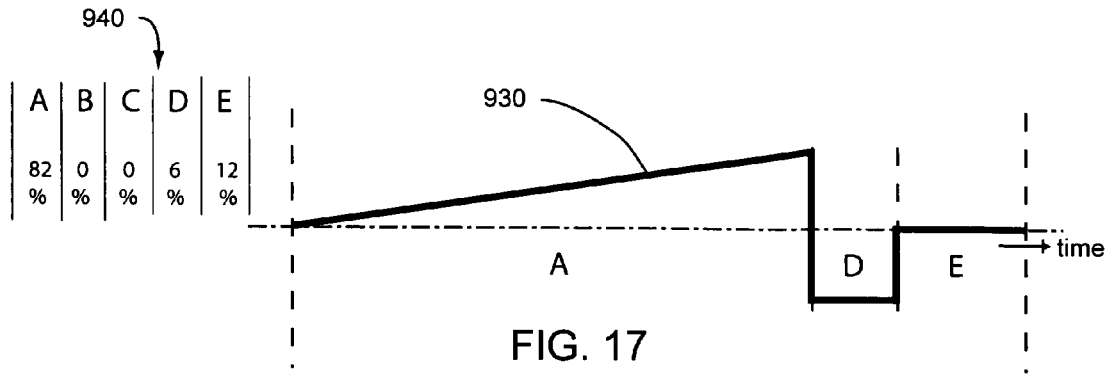
FIG. 17 is a drawing of a fourth alternate time graph of a sawtooth wave output embodiment of the system.

Referring to FIG. 15, typical low frequency square wave 890 is illustrated with low frequency square wave time duration table 920. FIG. 16 illustrates typical mid-frequency triangular wave 910 with low-frequency triangular wave time duration table 920. FIG. 17 illustrates typical high-frequency sawtooth wave 930 with high-frequency sawtooth wave time duration table 940.

While the instant invention has been shown and described herein in what are conceived to be the most practical and preferred embodiments, it is recognized that departures may be made therefrom within the scope of the invention, which is therefore not to be limited to the details disclosed herein, but is to be afforded the full scope of the claims so as to embrace any and all equivalent apparatus and articles.

What is claimed is:

1. A digital electromagnetic resonance therapy system for therapeutically treating disorders comprising:
   a digital electromagnetic pulse generator including a control unit comprising a microcontroller electrically connected to a power supply and a digital-to-analog converter, the digital-to-analog converter having at least two outputs, the control unit generating direct current and temporally-varying excitation waveforms at each output of the digital-to-analog converter,
   wherein each cycle of the excitation waveforms includes five time portions, A, B, C, D and E forming a total time period of T, portions A, B and C have a positive or zero amplitude and at least one portion includes a length of greater than zero, portion D has a negative amplitude and a length greater than zero and portion E has a zero amplitude and a length sufficient to allow all inductive energy dissipation prior to the next cycle;
   a plurality of low-frequency power amplifiers connected to the outputs of the digital-to-analog converters of the control unit, the low-frequency power amplifiers each having an input and an output;
   at least one air core electromagnetic coil connected to each of the outputs of the low-frequency power amplifiers;
   a current sensor monitoring the current supplied to the coil; and
   a temperature sensor limiting the temperature of the coil by modifying the excitation waveforms.

2. The system of claim 1 further including software algorithms to cause the control unit to issue the excitation waveforms as periodic trapezoidal, square, triangular and sawtoothed waveforms.

3. The system of claim 1 wherein the air core electromagnetic coil comprises an ocular coil within goggles for treatment of diseases and injuries of the eye.

4. The system of claim 1 wherein the electromagnetic coil is a tunnel antenna for use in the treatment of arm, leg, and hand injuries and diseases.

5. The system of claim 1 wherein the electromagnetic coil is an intra-cranial helmet for the treatment of brain injuries and diseases.

6. The system of claim 1 wherein the electromagnetic coil is a combination of a plurality of planar coil paddles arranged generally in pairs with an upward NORTH and a downward NORTH disposed flux direction for the treatment of lumbar and whole body diseases and injuries.

7. The system of claim 1 wherein the electromagnetic coil is a combination of two opposing planar coil paddles and a buttocks paddle for the treatment of urinary diseases and injuries.

8. A method of treating human injuries and diseases with a digital electromagnetic resonance therapy system comprising the steps of:
   providing the system of claim 1,
   placing the air core coil proximate to a diseased or injured region of a human body,
   interconnecting the electromagnetic coil to the electromagnetic pulse generator to produce the excitation waveforms and lines of magnetic flux from the electromagnet coil, and
   energizing the pulse generator to cause periodic electric currents to flow in the electromagnet coil, said magnetic flux creating Faraday currents within the body to heal the diseased or injured region.

9. The method of claim 8 further comprising the steps of: monitoring an internal coil temperature, and responding to the temperature sensor measurement to limit the power applied to the electromagnet coil in order to limit the internal temperature of the coil.

* * * * *